United States Patent
Greenleaf et al.

(10) Patent No.: US 11,058,398 B2
(45) Date of Patent: *Jul. 13, 2021

(54) SYSTEM AND METHOD FOR SHEAR WAVE ELASTOGRAPHY BY TRANSMITTING ULTRASOUND WITH SUBGROUPS OF ULTRASOUND TRANSDUCER ELEMENTS

(71) Applicant: Mayo Foundation for Medical Education and Research, Rochester, MN (US)

(72) Inventors: James F. Greenleaf, Rochester, MN (US); Shigao Chen, Rochester, MN (US); Pengfei Song, Rochester, MN (US); Armando Manduca, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

This patent is subject to a terminal disclaimer.

(21) Appl. No.: 16/023,782

(22) Filed: Jun. 29, 2018

(65) Prior Publication Data

US 2018/0317887 A1    Nov. 8, 2018

Related U.S. Application Data

(62) Division of application No. 14/397,395, filed as application No. PCT/US2013/063631 on Oct. 7, 2013, now Pat. No. 10,624,609.

(Continued)

(51) Int. Cl.
*A61B 8/08* (2006.01)
*A61B 8/00* (2006.01)
(Continued)

(52) U.S. Cl.
CPC ............ *A61B 8/485* (2013.01); *A61B 8/08* (2013.01); *A61B 8/4488* (2013.01);
(Continued)

(58) Field of Classification Search
CPC ......... A61B 8/08; A61B 8/485; A61B 8/4488; A61B 8/4494; A61B 8/5223
See application file for complete search history.

(56) References Cited

U.S. PATENT DOCUMENTS

| 6,371,912 B1* | 4/2002 | Nightingale ......... A61B 5/0053 600/437 |
| 2010/0222678 A1* | 9/2010 | Bercoff .................... A61B 8/08 600/442 |

(Continued)

FOREIGN PATENT DOCUMENTS

| WO | 2011064688 A1 | 6/2011 |
| WO | 2012085812 A2 | 6/2012 |
| WO | 2012/116364 A1 | 8/2012 |

OTHER PUBLICATIONS

Manduca et al., "Spatio-temporal directional filtering for improved inversion of MR elastography images", Med Image Anal. Dec. 2003;7(4):465-73.*

(Continued)

*Primary Examiner* — Christopher L Cook
(74) *Attorney, Agent, or Firm* — Quarles & Brady LLP

(57) ABSTRACT

Systems and methods for performing shear wave elastography using push and/or detection ultrasound beams that are generated by subsets of the available number of transducer elements in an ultrasound transducer. These techniques provide several advantages over currently available approaches to shear wave elastography, including the ability to use a standard, low frame rate ultrasound imaging system and the ability to measure shear wave speed throughout the (Continued)

entire field-of-view rather than only those regions where the push beams are not generated.

10 Claims, 5 Drawing Sheets

Related U.S. Application Data

(60) Provisional application No. 61/710,744, filed on Oct. 7, 2012.

(51) Int. Cl.
    *G01S 7/52*     (2006.01)
    *G01N 29/07*     (2006.01)
    *G01N 29/26*     (2006.01)
    *G01S 15/89*     (2006.01)

(52) U.S. Cl.
CPC .......... *A61B 8/4494* (2013.01); *A61B 8/5223* (2013.01); *G01N 29/07* (2013.01); *G01N 29/262* (2013.01); *G01S 7/5209* (2013.01); *G01S 7/52022* (2013.01); *G01S 7/52042* (2013.01); *G01S 15/8915* (2013.01); *G01S 15/8927* (2013.01); *G01N 2291/011* (2013.01); *G01N 2291/02475* (2013.01); *G01N 2291/02827* (2013.01); *G01N 2291/0422* (2013.01)

(56) References Cited

U.S. PATENT DOCUMENTS

| | | | |
|---|---|---|---|
| 2011/0063950 A1 | 3/2011 | Greenleaf et al. | |
| 2011/0066030 A1 | 3/2011 | Yao | |
| 2011/0184287 A1* | 7/2011 | McAleavey | G01S 7/52042 600/438 |
| 2011/0263978 A1 | 10/2011 | Chen et al. | |
| 2011/0319793 A1* | 12/2011 | Hynynen | A61N 7/02 601/2 |
| 2012/0065504 A1* | 3/2012 | Sandrin | A61B 8/08 600/438 |
| 2012/0095323 A1 | 4/2012 | Eskandari et al. | |
| 2013/0296698 A1* | 11/2013 | Fraser | A61B 8/4488 600/438 |

OTHER PUBLICATIONS

Japan Patent Office, Notification of Reason for Refusal, Application No. 2015-511818, dated Oct. 13, 2015.
International Search Report and Written Opinion dated Dec. 12, 2013 in connection with PCT/US2013/063631.

* cited by examiner

SYSTEM AND METHOD FOR SHEAR WAVE ELASTOGRAPHY BY TRANSMITTING ULTRASOUND WITH SUBGROUPS OF ULTRASOUND TRANSDUCER ELEMENTS

CROSS-REFERENCE TO RELATED APPLICATIONS

This application is a divisional of U.S. patent application Ser. No. 14/397,395 filed Oct. 27, 2014, which is the US National Phase of PCT/US13/63631 filed Oct. 7, 2013, which claims priority to U.S. Patent Application 61/710,744 filed Oct. 7, 2012, the entirety of all of which are incorporated by reference herein for all purposes.

STATEMENT REGARDING FEDERALLY SPONSORED RESEARCH

This invention was made with government support under EB002167 and DK082408 awarded by the National Institutes of Health. The government has certain rights in the invention.

BACKGROUND OF THE INVENTION

The field of the invention is systems and methods for ultrasound imaging. More particularly, the invention relates to systems and methods for shear wave elastography using ultrasound.

Shear waves can be used to evaluate the viscoelastic properties of tissue, which are sensitive biomarkers of tissue pathology. To perform two-dimensional ultrasound shear wave elastography, an ultrasound imaging system with a frame rate of several kilohertz is required to capture the fast moving shear waves. This is not feasible with conventional ultrasound imaging systems, which typically have a frame rate of less than 100 Hz and where two-dimensional images are formed line by line. Thus, it would be desirable to provide a system and method capable of performing two-dimensional shear wave elastography with a conventional ultrasound imaging system.

SUMMARY OF THE INVENTION

The present invention overcomes the aforementioned drawbacks by providing a method for measuring a mechanical property of an object using an ultrasound system having an ultrasound transducer that includes a plurality of transducer elements. At least one shear wave is induced in the object, and elastography data is obtained from the object. The elastography data is obtained by dividing the transducer elements in the ultrasound transducer into a plurality of subgroups of transducer elements; successively transmitting a set of ultrasound beams using a different subgroup of transducer elements, thereby successively transmitting ultrasound to different regions in the object; and repeating that process at a pulse repetition frequency such that each set of ultrasound beams is effectively repeated at the pulse repetition frequency. From the obtained elastography data, a mechanical property of the object can then be calculated.

It is another aspect of the invention to provide a method for measuring a mechanical property of an object using an ultrasound system having an ultrasound transducer that includes a plurality of transducer elements. At least one shear wave is induced in the object by dividing the transducer elements in the ultrasound transducer into a plurality of subgroups of transducer elements and transmitting a plurality of focused ultrasound beams, each focused ultrasound beam being transmitted by a single subgroup of transducer elements. Elastography data is obtained from the object by transmitting a detection ultrasound beam into the object and receiving echo signals in response thereto. A mechanical property of the object can then be calculated using the obtained elastography data.

The foregoing and other aspects and advantages of the invention will appear from the following description. In the description, reference is made to the accompanying drawings which form a part hereof, and in which there is shown by way of illustration a preferred embodiment of the invention. Such embodiment does not necessarily represent the full scope of the invention, however, and reference is made therefore to the claims and herein for interpreting the scope of the invention.

DETAILED DESCRIPTION OF THE INVENTION

Described here are systems and methods for performing shear wave elastography using push and/or detection ultrasound beams that are generated by subsets of the available number of transducer elements in an ultrasound transducer. These techniques provide several advantages over currently available approaches to shear wave elastography, including the ability to use a standard, low frame rate ultrasound imaging system and the ability to measure shear wave speed throughout the entire field-of-view rather than only those regions where the push beams are not generated.

High-end, conventional ultrasound imaging systems can image several lines from a single transmission using parallel beam forming. The pulse repetition frequency ("PRF") and pulse repetition interval ("PRI") for ultrasound imaging are determined by the maximum depth of the image. Assuming an imaging depth of 30 mm, the round-trip ultrasound travel time is $$\frac{2 \cdot 30[\text{mm}]}{1.54\left[\frac{\text{mm}}{\mu s}\right]} = 39[\mu s]. \quad (1)$$

Adding beam forming and other overhead time delay, a PRI of 50 μs (PRF=20 kHz) is feasible. The inventors have discovered that for two-dimensional shear wave elastography, the detection PRF at each spatial location can be less than 1 kHz. That is to say, using 1 kHz as an example, it is sufficient to perform shear wave elastography detection at the same spatial location only once every 1000 microseconds. Therefore, shear wave elastography can be performed using parallel beam forming detection at multiple locations sequentially while maintaining a PRF of 1 kHz at each location.

Figure 1:
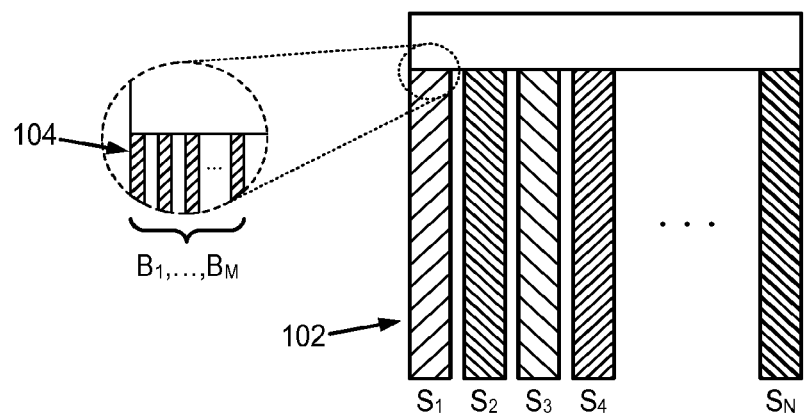
FIG. 1 is an illustration of a plurality of ultrasound beam sets, each containing a plurality of ultrasound beams, being transmitted by an ultrasound transducer.

Referring now to FIG. 1, an example of a sequence of ultrasound beams generated by an ultrasound system to produce a desired PRF at each spatial location is illustrated. For example, the sequence of ultrasound beams includes N sets, $S_1$, K, $S_N$ 102 each of M beams, $B_1$, K, $B_M$ 104 formed in parallel. This sequence is then repeated at the pulse repetition frequency for a number, P, of desired repetitions.

By way of example, each set, $S_n$, of ultrasound beams may include a plurality of beams, $B_m$, that are formed in parallel. For example, each set of ultrasound beams may include four beams formed in parallel and twenty beam sets may be used for a total sampling of eighty different locations during each pulse sequence. Using this approach, shear wave motion can be detected within a two-dimensional region covered by the M·N spatial locations with an effective PRF of 1 kHz at each spatial location. Assuming a line spacing of 0.3 mm, which is typical for a 5 MHz linear array ultrasound transducer, two-dimensional shear wave elastography can be performed within an area that is 30 mm deep and 24 mm wide using this technique. In other implementations, each set of ultrasound beams may include only a single ultrasound beam. As a result, the region-of-interest in which mechanical properties can be measured will be smaller than with parallel beam forming.

Figure 2:
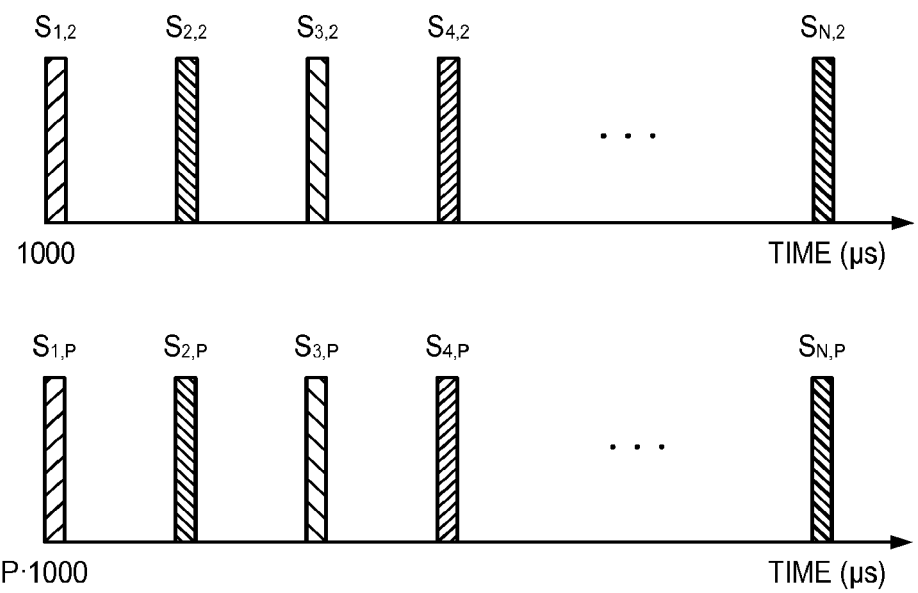
FIG. 2 is an example of a pulse timing diagram using the plurality of ultrasound beam sets of FIG. 1.

An example pulse sequence timing for P repetitions of the pulse sequence illustrated in FIG. 1 is illustrated in FIG. 2. At time t=0 μs, transmission of beam set $S_{1,1}$ is used to track shear wave motion at beam locations defined by the beams, $B_m$, that form beam set $S_{1,1}$. For example, when beam set $S_{1,1}$ is composed of four beams, shear wave motion at four locations will be tracked. At a preset time after beam set $S_{1,1}$ is generated, beam set $S_{2,1}$ is generated to detect shear wave motion occurring at beam locations defined by the beams, $B_m$, that form beam set $S_{2,1}$. For example, the preset time may be 50 microseconds. In the next cycle of the transmission, the first beam set is again transmitted. This beam set, $S_{1,2}$, is therefore transmitted at time t=1000 μs for a PRF of 1 kHz. The pulse sequence is repeated until the $P^{th}$ repetition is performed at time t=P·1000 μs.

The size of the two-dimensional shear wave elastography region is determined by the parallel beam forming capability of the ultrasound system and the required PRF at each spatial location. For example, six-beam parallel detection can allow a 36 mm image width if everything else does not change. It is contemplated that the required PRF may be higher in stiffer tissues. In this instance, the two-dimensional shear wave elastography region will be reduced in size in order to sustain the higher PRF. Therefore, implementations on traditional imagers may end up with a region-of-interest whose size changes with different applications. This result is similar to current two-dimensional color imaging methods in ultrasound scanners.

It is noted that although the descriptions provided above are made with respect to a one-dimensional array transducer, the concepts are also readily applicable to transducers with higher dimension, such as a two-dimensional array transducers.

It is noted that even though the PRF at each location is 1 kHz, different locations are sampled at different time grids. Referring to FIG. 2, the four beam locations in beam sets $S_{1,p}$ are sampled at times $$t=0,1000,2000,K,P·1000 \text{ μs}.$$

The beams in beam sets $S_{2,p}$ are sampled at times, $$t=50,1050,2050,K,(P·1000)+50 \text{ μs}.$$

This small time delay among locations needs to be accounted for in shear wave elastography reconstruction. Two example methods for accounting for this delay time are provided below.

Figure 3:
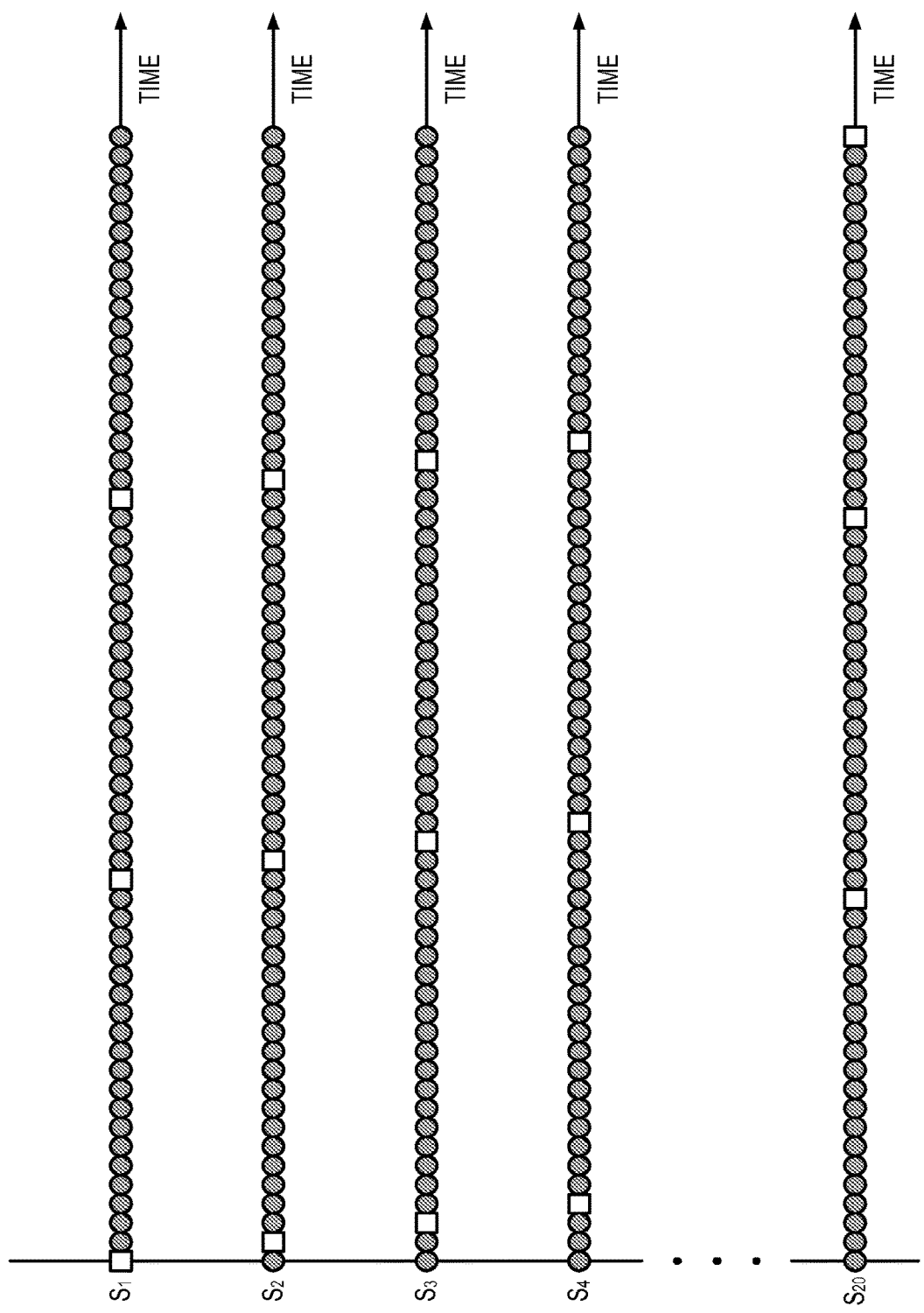
FIG. 3 is an example of aligning the time grids of different ultrasound beam sets using interpolation.

One example method for compensating for the delay time noted above is to interpolate the time signal at each location from PRF to N·PRF (e.g., from 1 kHz to 20 kHz) and to use the same time grid for all locations. As shown in FIG. 3, the squares represent the time instances of ultrasound detection at locations covered by beam sets $S_1$ to $S_N$. Each beam is sampled at a PRF of 1 kHz, but there is a time shift of 50 μs between adjacent beams. With interpolation back to 20 kHz for each beam, the time grids for each beam are aligned and synchronized. The interpolated points are represented by filled circles in FIG. 3.

Figure 4:
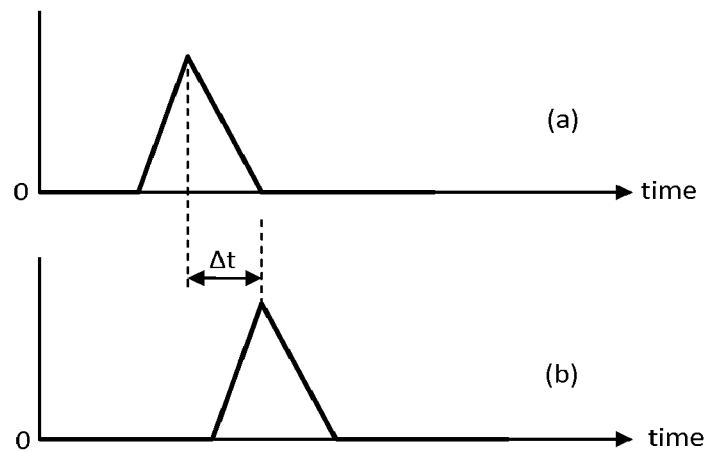
FIG. 4 is an example of a delay time in a shear wave front.

Referring to FIG. 4, the triangular waves in (a) and (b) represent the shear wave signals detected at two locations x and y after interpolation such that both signals start at the same time. Direction x→y is the direction of shear wave propagation. The time delay, Δt, of the shear wave between (a) and (b) can be calculated using time-to-peak, cross-correlation, or other methods. The shear wave speed can therefore be calculated by $$c_s = \frac{|y-x|}{\Delta t}; \tag{2}$$

where |y−x| is the distance between location y and location x.

Figure 5:
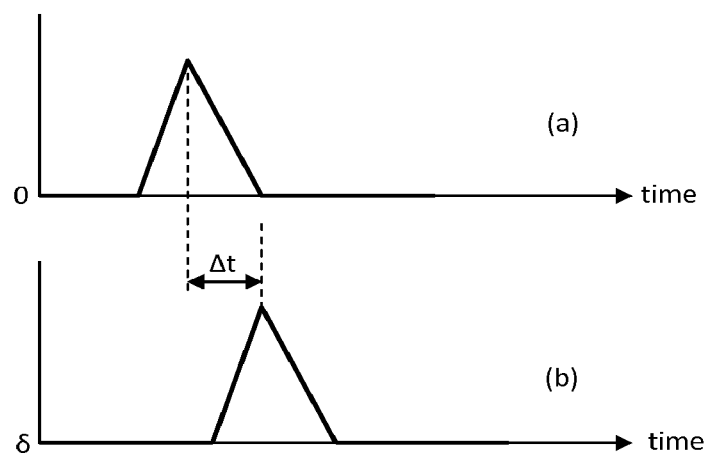
FIG. 5 is an example of another delay time in a shear wave front.

An example of another method for compensating for the delay time noted above is to account for the delay time when calculating the shear wave speed. Referring to FIG. 5, the triangular waves in (a) and (b) represent the shear wave signals detected at two locations, x and y, where the direction x→y is the direction of shear wave propagation. The time delay, Δt, of the shear wave between (a) and (b) can be calculated using time-to-peak, cross-correlation, or other methods. As explained above, the shear wave at different locations are detected at different time grids. Assuming that shear wave detection at location x starts at time t=0 as shown in (a), and shear wave detection at location y starts at time t=δ as shown in (b), the actual delay, ΔT, between the shear wave at locations x and y is $$\Delta T=(\Delta t+\delta) \tag{3}.$$

By way of example, if x is located at one of the beams in beam set $S_1$, and y is located at one of the beams in beam set $S_3$, then $$\delta=(3-1)·\Delta t=2·50=100 \text{ μs} \tag{4}.$$

The shear wave speed, $c_s$, can then be calculated by $$c_s = \frac{|y-x|}{\Delta T};\quad(5)$$

where |y−x| is again the distance between location y and location x.

It is noted that tracking beam sets $S_1$, K, $S_N$ do not need to be in a spatially sequential order; instead, the tracking beam sets can be placed in different spatial orders. For example, tracking beams set $S_1$ can be placed on left end of the image, whereas tracking beam set $S_2$ can be placed at right end of the image, with odd-numbered beam sets following sequentially inward to the center of the image from beam set $S_1$ and even-numbered beam sets following sequentially inward to the center of the image from beam set $S_2$.

In addition, two or more beam sets can be transmitted simultaneously to reduce the number of transmit-detection events required to cover a two-dimensional region of desired size. This approach has the benefit of increasing the effective PRF of detection at each beam set location. For example, beam sets $S_1$ and $S_{10}$ can be transmitted and detected simultaneously, followed by beam sets $S_2$ and $S_{11}$ simultaneously, until all N beam sets are covered. This process can repeat again in time.

It is also noted that each of the beam sets will be transmitted by a group of transducer elements. Different beam sets may have same or different transducer elements. For example, in a linear array or curved array ultrasound transducer, elements 1 through 32 may be used for beam set $S_1$, and elements 8 through element 40 may be used for beam set $S_2$, and so on. In another example of a phase array transducer with 64 elements, the same 64 elements may be used to transmit all beam sets from $S_1$ to $S_N$ by steering different beam sets to cover different regions.

The above teaching is for calculating the shear wave speed by measuring the time delay between shear waves detected at two or more locations along the shear wave propagation direction. The same concept can be applied for other methods of shear wave elasticity imaging, such as direct inversion and frequency dependent dispersion analysis. In addition, this method can be applied to shear waves produced by physiological motion, such as cardiac motion; mechanical vibration; and ultrasound radiation forces from single focused beams, single unfocused beams, multiple focused beams, or multiple unfocused beams.

Having described applications for transmitting ultrasound detection beams using subsets of the available transducer elements in an ultrasound transducer, techniques for using subsets of transducer elements to deliver ultrasound push beams are now discussed.

When an ultrasound push beam is transmitted into an object, shear waves are generated and propagate outward from the push beam in opposite directions. Consequently, shear waves are not generated in the push beam region, which means that shear wave speeds cannot be measured in the region where the push beam is generated. In addition, shear waves produced by an ultrasound push beam attenuate quickly over a short propagation distance. As a result, shear waves produced by a single push beam can only image a small region-of-interest; thus, in these instances, multiple push-detect acquisitions are required to piece together an image with large field-of-view ("FOV").

As described in co-pending PCT Application Publication WO2012/116364, entitled "Ultrasound Vibrometry with Unfocused Ultrasound," which is herein incorporated by reference in its entirety, a comb-shaped set of unfocused ultrasound beams can be used to provide a full FOV, two-dimensional shear wave speed map together with one rapid data acquisition. This method is referred to as comb-push ultrasound shear elastography ("CUSE").

In CUSE, multiple unfocused ultrasound push beams are used to produce shear waves within a tissue for shear wave elasticity imaging. Only one subset of transducer elements is used for each push beam; thus, multiple subsets of elements can be used for different spatial locations to simultaneously transmit multiple push beams. In CUSE, shear waves produced by each push beam can be treated as an independent realization of a single push beam.

Using CUSE, shear waves from different push beams interfere with each other and eventually fill the entire field-of-view ("FOV"). To achieve robust shear wave speed estimation, a directional filter can be used to extract left-to-right ("LR") propagating shear waves and right-to-left ("RL") propagating shear waves from the interfering shear wave patterns. A time-of-flight based shear wave speed estimate method may be used to recover local shear wave speed at each pixel from both LR waves and RL waves. A final shear wave speed map may then be combined from the LR speed map and RL speed map. Because comb-push pulses produce shear wave motions with high amplitude at all image pixels, including at the push beam areas, both shear wave speed at the "source free" areas and shear wave speeds at the push beam areas can be recovered.

Thus, CUSE enables a full FOV two-dimensional reconstruction of a shear elasticity map with only one data acquisition. To improve acoustic radiation force penetration and generate stronger shear waves into deeper tissue (i.e., liver and kidney), the previous CUSE method can be modified using focused ultrasound push beams. Using focused ultrasound push beams facilitates the generation of strong shear waves at locations deep within tissues. This ability to generate strong shear waves at deep tissue locations can lead to higher SNR for shear wave elasticity imaging compared to CUSE with unfocused beams.

Figure 6:
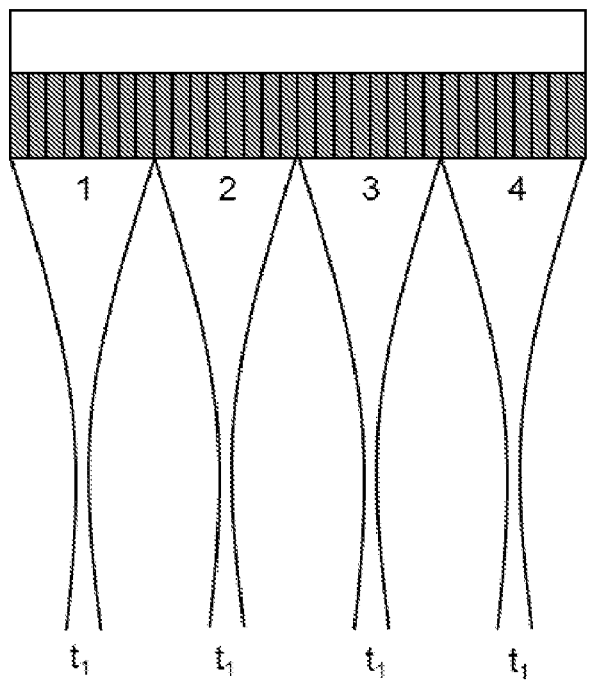
FIG. 6 is an illustration of a plurality of focused ultrasound push beams being simultaneously transmitted in a comb pattern.

In one configuration, illustrated in FIG. 6, the transducer elements are divided into a number of subgroups, such as four subgroups, that each simultaneously transmits a focused ultrasound beam. This technique is referred to as focused CUSE, or "F-CUSE." As noted, in F-CUSE, the transducer elements are divided into a number, N, of subgroups, with each subgroup containing one or more transducer elements.

As one example of the F-CUSE technique, a 128 element ultrasound transducer can be divided into four subgroups of 32 transducer elements each. In F-CUSE, all subgroups transmit focused ultrasound beams simultaneously to form a comb-push pattern ultrasound field. In one example, the duration of the push pulse beams can be on the order of 600 µs.

In another configuration, the transducer elements are divided into a number of subgroups with overlapping elements, and the subgroup that is used to transmit an ultrasound beam is rapidly changed along the lateral direction. The result of this "marching" of the subgroup of transducer elements being energized is to provide a focused ultrasound push beam at successively different horizontal locations. This technique may be referred to as marching CUSE, or "M-CUSE."

Figure 7:
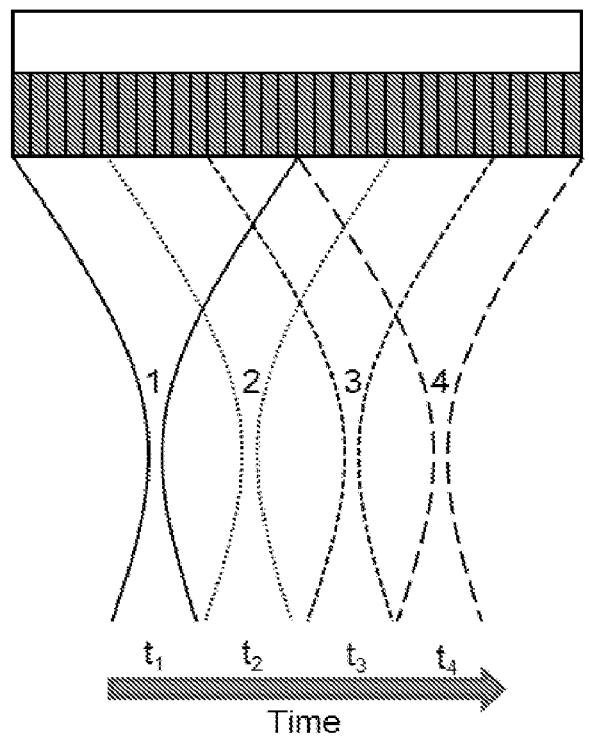
FIG. 7 is an illustration of a focused ultrasound push beam that is rapidly translated along a lateral direction to generate shear waves.

As one example of the M-CUSE technique, shown in FIG. 7, a 128 element ultrasound transducer can be divided into four, overlapping subgroups of 64 elements each. The first subgroup then transmits a single, focused push beam at a first time, t1. The duration of this push beam can be shorter than would be used in F-CUSE or traditional CUSE if it is desirable to control tissue or transducer heating due to repeated transmission using the overlapping transducer elements. As an example, the push beam duration in M-CUSE can be on the order of 200 µs. The push beam duration is selected based on considerations for how much overlap there is between subgroups of the transducer elements. For instance, the duration can be selected such that any given transducer element in overlapping subgroups is not energized for a consecutive duration that may lead to overheating in that element.

After the first push beam is transmitted, a second push beam is transmitted at a second time, t2, using the second subgroup of elements. This continues for the third and fourth subgroups. There is typically a small duration between consecutive push beams. For example, there can be a 15 µs delay between consecutive push beams. In this short duration of time, shear waves will propagate in soft tissue only about 0.45 mm, which is about 1.5 times the size of an individual transducer element in the transducer. Thus, in general, the amount of shear wave propagation between successive push beams is negligible for all subgroups after transmitting all of the focused push beams.

Figure 8:
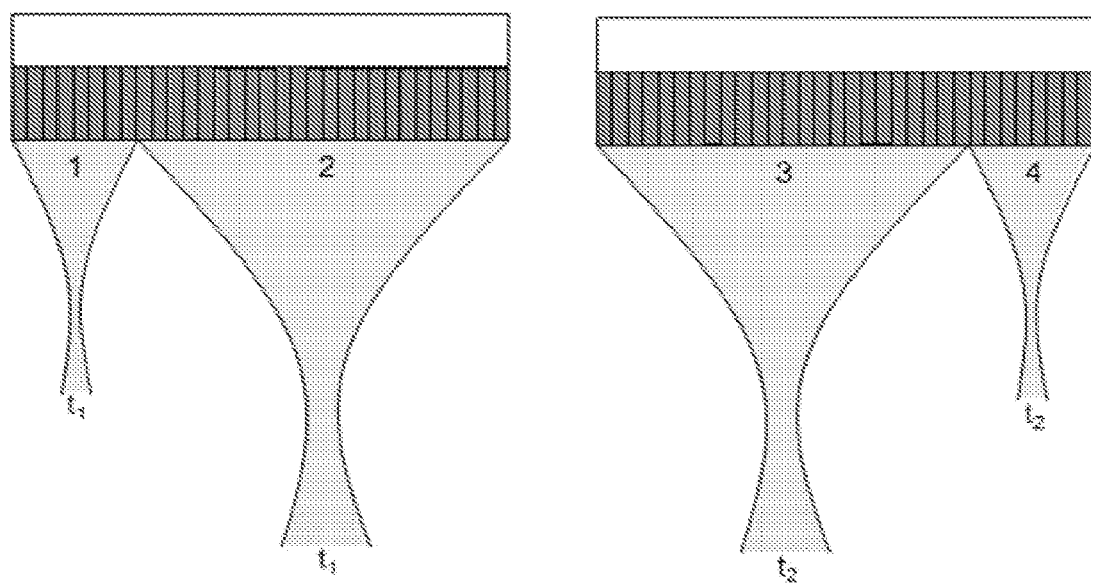
FIG. 8 is an illustration of a plurality of focused ultrasound push beams being simultaneously transmitted, in which each of the ultrasound push beams is generated with different sized subgroups of transducer elements.

It is noted that each push beam of the F-CUSE or M-CUSE techniques may have a different number of transmit elements and may be focused at different depths. Additionally, each of the push events for the M-CUSE technique may include using more than one push beams. In the example shown in FIG. 8, push beams 1 (with less elements) and 2 (with more elements) are simultaneously transmitted at time t1, followed by push beams 3 and 4 transmitted simultaneously at time t2. This combination push will produce strong shear waves at all depths and all lateral positions for shear wave detection and processing. It is also noted that push beams in M-CUSE can have different push durations and can be transmitted in an arbitrary order (for example, in a different order 1→4→3→2 compared to the order 1→2→3→4 illustrated in FIG. 7)

Similar to the original CUSE method, both F-CUSE and M-CUSE can generate comb-patterned ultrasound push beams that induce a complicated shear wave field with interferences. Directional filtering described by Manduca et al. in "Spatio-Temporal Directional Filtering for Improved Inversion of MR Elastography Images," *Medical Image Analysis,* 2003; 7(4): 465-473, can thus be used to separate the shear waves into multiple directions without interference so that robust shear wave estimates can be achieved at each imaging pixel within the FOV.

After comb-push transmission, a plane wave imaging mode can be used with all transducer elements delivering ultrasound to detect the propagating shear waves. Alternatively, the detection scheme described above can also be used.

The present invention has been described in terms of one or more preferred embodiments, and it should be appreciated that many equivalents, alternatives, variations, and modifications, aside from those expressly stated, are possible and within the scope of the invention.

The invention claimed is:

1. A method for measuring a mechanical property of an object using an ultrasound system having an ultrasound transducer that includes a plurality of transducer elements, the steps of the method comprising:
   a) controlling the ultrasound transducer to energize a plurality of subgroups of transducer elements to transmit a corresponding plurality of different focused ultrasound beams each focused at a different lateral location and each transmitted at a different time, thereby inducing multiple different shear waves in the object;
   b) for each different lateral location, obtaining elastography data representative of the multiple different shear waves by transmitting at least one detection ultrasound beam into the object and receiving echo signals in response thereto;
   c) generating processed elastography data by processing the obtained elastography data to separate the multiple different shear waves into multiple different directional components to reduce effects of interference between the multiple different shear waves; and
   d) calculating a mechanical property of the object using the processed elastography data.

2. The method as recited in claim 1, wherein at least some successively transmitted focused ultrasound beams are generated in step a) by spatially adjacent subgroups of transducer elements.

3. The method as recited in claim 1, wherein at least some successively transmitted focused ultrasound beams are generated in step a) by spatially overlapping subgroups of transducer elements.

4. The method as recited in claim 1, wherein step b) includes:
   i) dividing the transducer elements in the ultrasound transducer into a plurality of subgroups of transducer elements;
   ii) successively transmitting a set of ultrasound beams using a different subgroup of transducer elements, thereby successively transmitting ultrasound to different regions in the object;
   iii) repeating step ii) at a pulse repetition frequency such that each set of ultrasound beams is effectively repeated at the pulse repetition frequency.

5. The method as recited in claim 1, wherein step c) includes applying a directional filter to the elastography data.

6. The method as recited in claim 1, wherein step a) includes transmitting at least some of the plurality of different focused ultrasound beams to focus at different depth locations than other ones of the plurality of different focused ultrasound beams.

7. The method as recited in claim 1, wherein the plurality of different focused ultrasound beams are transmitted in sequential sets, wherein each set contains multiple simultaneously generated focused ultrasound beams that are focused at different locations.

8. The method as recited in claim 1, wherein calculating the mechanical property in step d) includes using at least one of a time-to-peak method, a cross-correlation method, a direct inversion method, and a frequency dependent analysis method.

9. The method as recited in claim 1, wherein at least some of the plurality of focused ultrasound beams are transmitted for a longer duration than others of the plurality of focused ultrasound beams.

10. The method as recited in claim 1, wherein some of the plurality of subgroups of transducer elements include more transducer elements than others of the plurality of subgroups of transducer elements.

* * * * *